US010548735B2

(12) United States Patent
Servidio (10) Patent No.: US 10,548,735 B2
(45) Date of Patent: Feb. 4, 2020

(54) MODULAR HINGE KNEE PROSTHESIS AND IMPROVEMENTS OF SAME

(71) Applicant: Howmedica Osteonics Corp., Mahwah, NJ (US)

(72) Inventor: Damon J. Servidio, Towaco, NJ (US)

(73) Assignee: Howmedica Osteonics Corp., Mahwah, NJ (US)

(*) Notice: Subject to any disclaimer, the term of this patent is extended or adjusted under 35 U.S.C. 154(b) by 234 days.

(21) Appl. No.: 14/820,151

(22) Filed: Aug. 6, 2015

(65) Prior Publication Data

US 2017/0035572 A1 Feb. 9, 2017

(51) Int. Cl.
*A61F 2/38* (2006.01)
*A61F 2/30* (2006.01)

(52) U.S. Cl.
CPC ............ *A61F 2/3845* (2013.01); *A61F 2/385* (2013.01); *A61F 2002/3063* (2013.01); *A61F 2002/30331* (2013.01); *A61F 2002/30364* (2013.01); *A61F 2002/30471* (2013.01); *A61F 2002/30474* (2013.01); *A61F 2002/30626* (2013.01); *A61F 2002/30632* (2013.01); *A61F 2002/30934* (2013.01)

(58) Field of Classification Search
CPC ....... A61F 2/3836; A61F 2/384; A61F 2/3854
See application file for complete search history.

(56) References Cited

U.S. PATENT DOCUMENTS

| | | |
|---|---|---|
| 3,837,009 A | 9/1974 | Walker |
| 4,136,405 A | 1/1979 | Pastrick et al. |
| 4,219,893 A | 9/1980 | Noiles |
| 4,262,368 A | 4/1981 | Lacey |
| 4,301,553 A | 11/1981 | Noiles |
| 4,358,859 A | 11/1982 | Schurman et al. |
| 5,011,496 A | 4/1991 | Forte et al. |
| 5,358,527 A | 10/1994 | Forte |
| 5,370,701 A | 12/1994 | Finn |
| 5,413,607 A | 5/1995 | Engelbrecht et al. |
| 5,766,257 A | 6/1998 | Goodman et al. |

(Continued)

FOREIGN PATENT DOCUMENTS

| | | |
|---|---|---|
| EP | 0716839 A1 | 6/1996 |
| EP | 0724868 A1 | 8/1996 |

(Continued)

OTHER PUBLICATIONS

Biomet Orthopedics Inc., Resurfacing Distal Femur, OSS, Orthopaedic Salvage System, 2003.

(Continued)

*Primary Examiner* — Bruce E Snow
(74) *Attorney, Agent, or Firm* — Lerner, David, Littenberg, Krumholz & Mentlik, LLP (57) ABSTRACT

A total knee prosthesis including a tibial component having a baseplate portion and a protruding portion extending from the baseplate portion is disclosed. An axle is connectable to the tibial component directly or indirectly. A femoral component has an articular surface and an opening for receipt of the axle. The opening defines a pivot center about which the femoral prosthesis rotates. The articular surface has a posterior portion having a first flexion radius defining a first flexion center. The first flexion center is offset from the pivot center a distance substantially equal to a product of a constant and the first flexion radius.

22 Claims, 5 Drawing Sheets

(56) References Cited

U.S. PATENT DOCUMENTS

| | | |
|---|---|---|
| 5,800,552 A | 9/1998 | Forte |
| 5,824,096 A | 10/1998 | Pappas et al. |
| 5,954,770 A | 9/1999 | Schmotzer et al. |
| 6,013,103 A | 1/2000 | Kaufman et al. |
| 6,447,549 B1 | 9/2002 | Taft |
| 6,719,800 B2 | 4/2004 | Meyers et al. |
| 6,962,607 B2 | 11/2005 | Gundlapalli et al. |
| 7,387,644 B2 | 6/2008 | Beynnon et al. |
| 7,572,292 B2 | 8/2009 | Crabtree et al. |
| 7,591,855 B2 | 9/2009 | Keller |
| 7,658,767 B2 | 2/2010 | Wyss |
| 7,695,520 B2 | 4/2010 | Metzger et al. |
| 7,708,782 B2 | 5/2010 | Burstein et al. |
| 7,871,442 B2 | 1/2011 | Servidio |
| 7,918,893 B2 | 4/2011 | Romeis et al. |
| 7,998,218 B1 | 8/2011 | Brown |
| 8,163,028 B2 | 4/2012 | Metzger et al. |
| 8,268,006 B2 | 9/2012 | Meyers et al. |
| 8,328,873 B2 | 12/2012 | Metzger et al. |
| 8,382,848 B2 | 2/2013 | Ries et al. |
| 8,523,950 B2 | 9/2013 | Dees et al. |
| 8,545,570 B2 | 10/2013 | Crabtree et al. |
| 8,545,571 B2 | 10/2013 | Collazo et al. |
| 8,568,485 B2 | 10/2013 | Ries et al. |
| 8,617,250 B2 | 12/2013 | Metzger |
| 8,628,579 B2 | 1/2014 | Ries et al. |
| 9,283,081 B2 | 3/2016 | Bartels et al. |
| 2004/0249467 A1 | 12/2004 | Meyers et al. |
| 2005/0246028 A1 | 11/2005 | Pappas et al. |
| 2011/0270403 A1 | 11/2011 | Ries et al. |
| 2012/0271427 A1 | 10/2012 | Serafin, Jr. et al. |
| 2012/0330430 A1 | 12/2012 | Meyers et al. |
| 2013/0190883 A1 | 7/2013 | Collard et al. |
| 2013/0325135 A1 | 12/2013 | Crabtree, Jr. et al. |
| 2014/0025172 A1 | 1/2014 | Lucas et al. |
| 2014/0025174 A1 | 1/2014 | Lucas et al. |
| 2014/0114318 A1 | 4/2014 | May et al. |

FOREIGN PATENT DOCUMENTS

| | | |
|---|---|---|
| FR | 2980104 A1 | 3/2013 |
| WO | 03/059203 A1 | 7/2003 |
| WO | 2013/003433 A1 | 1/2013 |

OTHER PUBLICATIONS

DePuy Companies of Johnson & Johnson, S-ROM NOILES Surgical Technique, 2011.

Zimmer® NexGen® Rotating Hinge Knee Primary/Revision, 2002.

Stryker Howmedica Osteonics, Modular Roating Hinge Knee System, 2000.

European Search Report in EP16182774, dated Jan. 4, 2017, 3 pages.

MODULAR HINGE KNEE PROSTHESIS AND IMPROVEMENTS OF SAME

BACKGROUND OF THE INVENTION

A natural knee includes a distal femur, proximal tibia, and patella. The distal femur and proximal tibia comprise a tibiofemoral joint, and the distal femur and patella comprise a patellofemoral joint. Soft tissue, such as ligaments and tendons, help stabilize these joints throughout flexion of the knee. However, the natural knee can become damaged or diseased. For example, osteoarthritis can destroy articular cartilage within the tibiofemoral and/or patellofemoral joints producing painful bone-on-bone articulation and malalignment of the knee.

Surgery may be indicated to treat complications of such damage or disease. This may involve resecting portions of the distal femur, proximal tibia, and patella and replacing the resected bone with one or more prostheses. Surgery to replace the patellofemoral and tibiofemoral joints is commonly referred to as total knee arthroplasty ("TKA") or total knee replacement.

In many circumstances, damage extends beyond the articular cartilage and bone further complicating a TKA procedure. For example, malalignment of the knee caused by osteoarthritis can impose excess stress on stabilizing soft tissue, which may result in damage and/or laxity of such structures and instability of the knee. Without resolution, such damage and/or laxity can compromise the replaced tibiofemoral and patellofemoral joints and reduce patient satisfaction.

Certain categories of prostheses have been developed to address soft tissue instability. One such category is a posterior stabilized ("PS") prosthesis. PS prostheses are often utilized to address posterior cruciate ligament deficiency in patients who otherwise have sufficient collateral ligament stability. Many of the existing PS prostheses offer tibiofemoral rotational freedom while providing stability during flexion to prevent femoral anterior subluxation. This is often achieved by a femoral cam and tibial post mechanism.

Another TKA prosthesis category is a hinge knee prosthesis. Hinge knee prostheses are typically indicated for patients that have significant stabilizing soft tissue deficiencies, particularly significant laxity or complete removal of the collateral ligaments. Many hinge knee prostheses offer a one-degree-of-freedom hinge about which the knee flexes and extends. This prosthesis category generally provides the most stability of any of the TKA prostheses. However, this often comes at the expense of being one of the most restrictive when it comes to natural knee kinematics.

Certain hinge knee prostheses have been developed to provide additional degrees of freedom to help mimic certain aspects of natural knee kinematics. However, such prostheses generally focus on articulation between the femur and tibia and have yet to solve patellofemoral kinematics. As a result, current hinge knee prostheses generally have unnatural patellofemoral kinematics when implanted which can be painful and restrict range of motion of the knee.

Therefore, further improvements are desirable.

BRIEF SUMMARY OF THE INVENTION

In one aspect of the present disclosure, a total knee prosthesis includes a tibial component having a baseplate portion and a protruding portion extending from the baseplate portion. An axle is connectable to the tibial component directly or indirectly. A femoral component has an articular surface and an opening for receipt of the axle. The opening defines a pivot center about which the femoral prosthesis rotates. The articular surface includes a posterior portion having a first flexion radius defining a first flexion center. The first flexion center is offset from the pivot center a distance substantially equal to a product of a constant and the first flexion radius.

Additionally, the constant may be 0.4. Also, the femoral component may have an anterior-posterior dimension defined by a distance between anterior and posterior extents of the prosthesis, and the first flexion radius may be substantially equal to one-third of the anterior-posterior dimension. The first flexion radius may be about 16-28 mm.

Continuing with this aspect, the protruding portion of the tibial component may define a longitudinal axis, and the pivot center may be about 15-25 mm from the longitudinal axis in an anterior-posterior direction when the tibial component and femoral component are coupled together via the axle. Baseplate portion may include a bone contact surface for contacting a proximal tibial resected surface. The bone contact surface may be about 35-55 mm from the pivot center in a superior-inferior direction when the tibial component and femoral component are coupled together via the axle.

Furthermore, the first flexion center may be positioned such that a line segment intersecting the pivot center and first flexion center is substantially parallel to a patella tendon when the total knee prosthesis is implanted and articulated to about 90 degrees of flexion. The articular surface may include an anterior portion having a second flexion radius defining a second flexion surface. The first flexion center may be about 7-21 mm offset in the sagittal plane from the second flexion center. The pivot center, first flexion center, and second flexion center may form vertices of a triangle having a hypotenuse extending between the pivot center and second flexion center, a first line segment extending between the pivot center and first flexion center, and a second line segment extending between the first and second flexion centers. An angle formed between the first line segment and hypotenuse may be about 15-60 degrees. The hypotenuse may be about 15-35 mm.

Also, a reference angle formed between the first line segment and a line intersecting the pivot center and a tibial tubercle of the tibia determines a patellar tilt angle of a patella about the tibial tubercle with respect to a superior-inferior axis of the tibia. The reference angle and patellar tilt angle may be substantially equal. The reference angle is about 35 degrees or less.

Moreover, the total knee prosthesis may also include a coupling component having a bearing, a head portion, and an articulating portion. The bearing may be receivable by the tibial component. The head portion may be to the femoral component and may have an opening extending therethrough for receipt of the axle. The articulating portion may be disposed between the head portion and bearing and have a curved inferior surface for sliding articulation with a superior surface of the tibial component.

In another aspect of the present disclosure, a total knee prosthesis includes a tibial component for implantation into a tibia of a knee joint. A coupling component is configured to engage the tibial component and has a head portion defining an opening therethrough for receipt of an axle. A femoral component for implantation into a femur of a knee joint defines a recess for receipt of the head portion and a transverse opening for receipt of the axle and has an articular surface having a first curved portion and a second curved portion. The opening defines a pivot center about which the femoral component flexes and extends. The first curved portion defines a first radius and a first center. The second curved portion defines a second radius and a second center. The pivot center and first and second centers are positioned with respect to each other such that when the total knee prosthesis is implanted into the knee joint, the articular surface is positioned with respect to a tibial tubercle of the tibia such that a tilt angle of a patella about the tibial tubercle achieves and maintains about 35 degrees or less with respect to a superior-inferior axis of the tibia as the patella articulates with the articular surface through flexion of the femoral component relative to the tibial component of between 90 and 135 degrees.

Additionally, the first center may be offset from the pivot center in a sagittal plane a distance substantially equal to a product that is a function of the flexion radius. The product may be the flexion radius multiplied by 0.4. The second center may be offset from the pivot center in a sagittal plane a distance substantially equal to 15-35 mm. The first center and second center may be offset from one another a distance substantially equal to 7-21 mm.

In another aspect of the present disclosure, a total knee prosthesis includes a tibial component having a baseplate portion and a protruding portion extending from the baseplate portion. An axle is connectable to the tibial component directly or indirectly. A femoral component has an articular surface and an opening for receipt of the axle. The opening defines a pivot center about which the femoral prosthesis rotates. The articular surface has a posterior portion having a first flexion radius defining a first flexion center. The first flexion radius is substantially equal to one-third of an anterior-posterior width of the femoral component.

In a further aspect, a knee prosthesis assembly includes a tibial component, a bearing bushing, a tibial insert, a bearing component, an axle and a femoral component. The tibial component includes an opening for receipt of the bearing bushing. The bearing bushing includes an opening extending therein along a longitudinal axis thereof. The tibial insert includes a concave articular surface and an opening extending therethrough. The bearing component includes an articulating portion having a convex articular surface corresponding to the concave articular surface of the tibial insert. The bearing component also includes a bearing extending from the articulating portion, which is configured to be rotatably disposed within the bearing bushing. The bearing component also includes a head portion extending from the articulating portion in a direction opposite that of the bearing. The head portion includes an opening extending therethrough for receipt of the axle. The femoral component also has an articular surface and transverse openings extending through the femoral component in a lateral-medial direction. The transverse openings are aligned and sized to receive the axle therein. The femoral component also includes a recess extending through a posterior end of the femoral component such that the recess intersects the transverse openings. The articular surface of the femoral component is positioned relative to an axis of the transverse opening such that when knee prosthesis is assembled, a patella tracking along the articular surface can tilt about a tibial tubercle up to 35 degrees or less from an extension position thereof.

Additionally, the assembly may include a bumper having a bumper portion and a bumper extension extending therefrom. The bumper extension may be elongate and configured to fit within an opening within the head portion of the bearing component. The bumper portion may have a bumper surface configured to absorb contact with the femoral component in hyperextension. Also, the assembly may include a pair of axle bushings having flanges at one end thereof and configured to at least partially fit within the transverse openings and having an axle opening extending therein for receipt of the axle.

Continuing with this aspect, the concave articular surface of the tibial component may be curved in a sagittal plane and may slope from an anterior extent and posterior extent thereof to a location between the anterior and posterior extents.

In yet another aspect of the present disclosure, a method of implantation of a knee prosthesis includes resecting a proximal tibia and implanting a tibial component onto the tibia such that a baseplate of the tibial component rests on a proximal resected surface of the tibia. The method also includes inserting a bearing bushing into an opening in the tibial component and attaching a tibial insert to the baseplate. Also included in the method is inserting an elongate bearing of a bearing component through an opening in the tibial insert and into an opening of the bearing bushing, which is positioned within the tibial component, until articular surfaces of the bearing component contact corresponding articular surfaces of the tibial insert.

A femur is resected forming at least three resected surfaces. A femoral component is attached to the at least three resected surfaces via at least three inner surfaces of the femoral component. The femoral component is mounted to a head portion of the bearing component such that transverse openings of the femoral component align with an opening in the head portion. An axle is inserted through the transverse openings and head portion opening. A patella is slidingly coupled to an articular surface of the femoral component.

The articular surface of the femoral component has an anterior portion and posterior portion. The posterior portion is positioned along the articular surface of the femoral component such that the patella contacts and articulates with the posterior portion in 115 degrees or more of flexion of the tibial component relative to the femoral component about a pivot axis defined by the axle. The posterior portion of the femoral component articular surface defines a flexion circle having a flexion center. The flexion center is positioned relative to the pivot axis such that when the patella articulates along the posterior portion, the patella is prohibited from tilting beyond 35 degrees from a starting extension position.

BRIEF DESCRIPTION OF THE DRAWINGS

The features, aspects, and advantages of the present disclosure will become better understood with regard to the following description, appended claims, and accompanying drawings in which:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart, and the term "distal" means more distant from the heart. The term "inferior" means toward the feet, and the term "superior" means toward the head. The term "anterior means toward the front of the body or the face, and the term "posterior" means toward the back of the body. The term "medial" means toward the midline of the body, and the term "lateral" means away from the midline of the body. Also, as used herein, the terms "about," "generally" and "substantially" are intended to mean that deviations from absolute are included within the scope of the term so modified.

Figure 1:
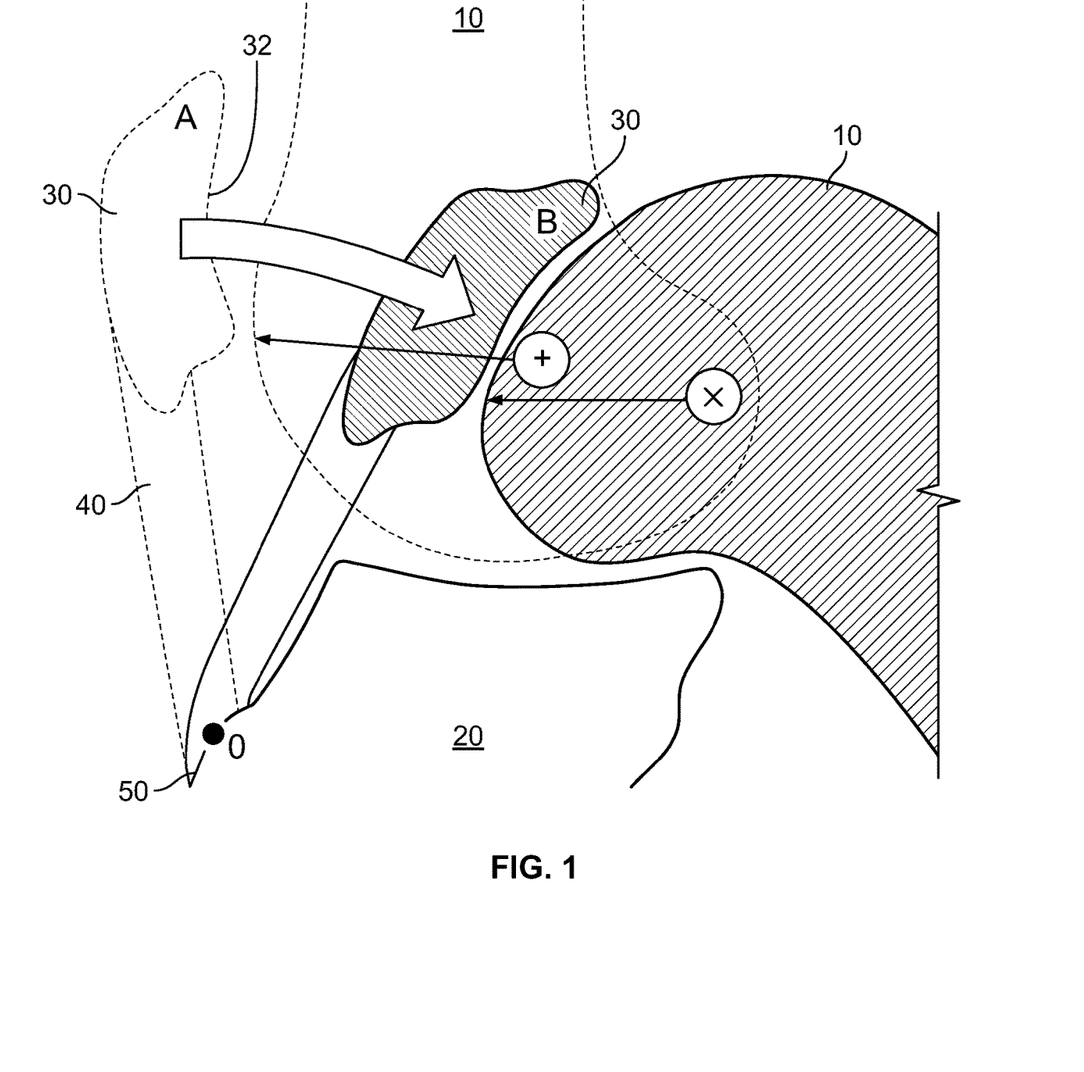
FIG. 1 is schematic view of the natural articulation of a patellofemoral joint from extension to deep flexion of a knee.

FIG. 1 illustrates sagittal plane kinematics of a natural knee, particularly a patellofemoral joint, as a tibia 20 flexes relative to a femur 10 from full extension to deep flexion. As used herein, "deep flexion" refers to a flexion angle substantially equal to or greater than 115 degrees.

As shown, patella 30 is connected on a distal side thereof to a patella tendon 40, which itself is connected to a tibial tubercle 50 at point O. As tibia 20 flexes relative to femur 10, patella 40 articulates along a trochlear groove of femur 10 and rotates about point O from its starting extension position A to its maximum flexion position B. During this movement, patella 40 tilts to a maximum angle relative to extension position A of about 35 degrees in such a way that a deep surface 32 thereof, which faced posteriorly at extension position A, faces posteriorly and inferiorly in flexion position B.

Patella 30 generally reaches this maximum tilt angle of about 35 degrees once tibia 20 and femur 10 reach deep flexion. Thus, in a natural knee, once a knee reaches about 115 degrees of flexion, patella 30 is tilted at about 35 degrees relative to an extension position and does not go beyond that tilt angle even when the knee is flexed beyond 115 degrees. However, it should be understood that the maximum tilt angle may vary from person to person and may increase or decrease slightly during articulation through deep flexion.

Figure 2:
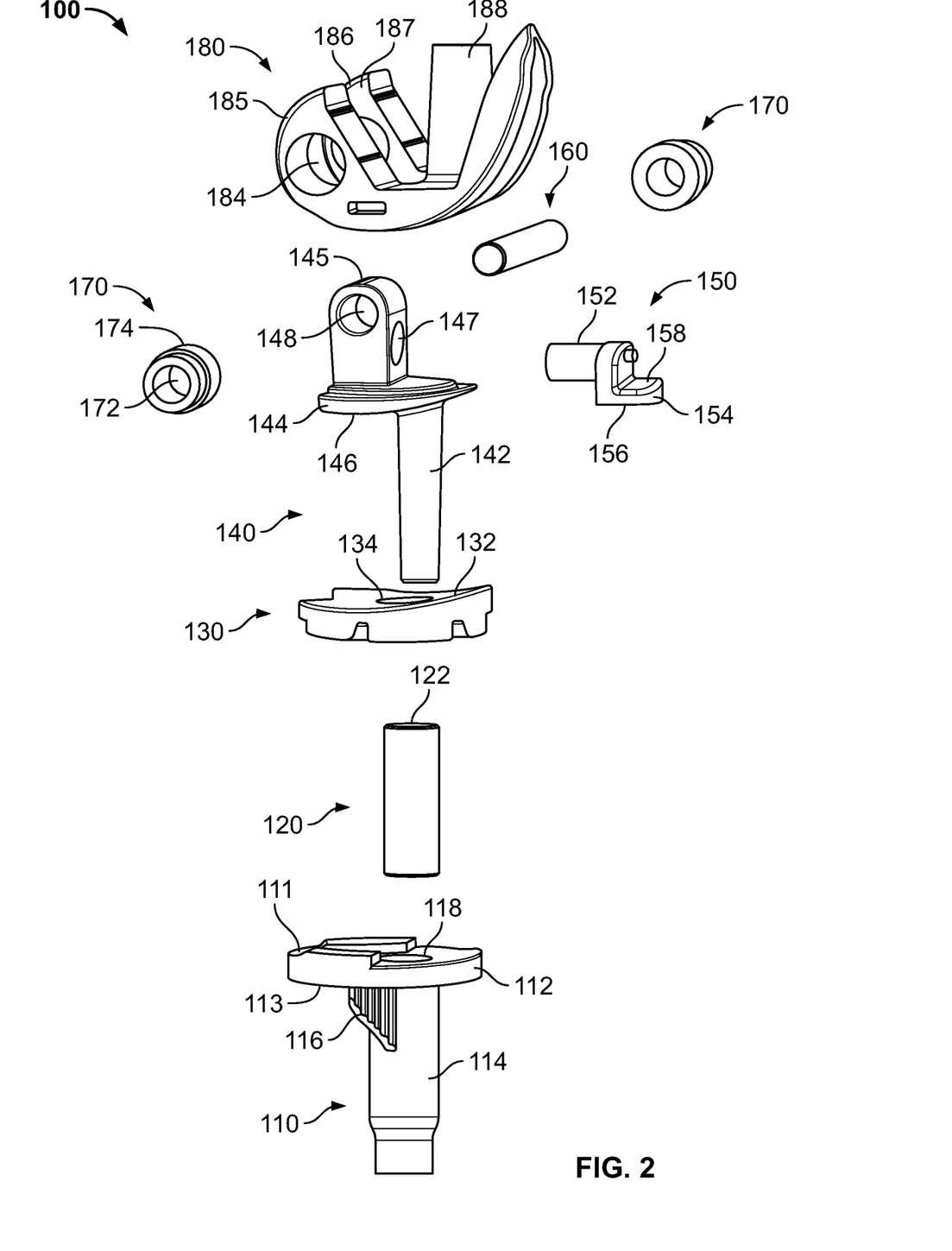
FIG. 2 is an exploded view of a total knee prosthesis according to the present invention.

FIG. 2 depicts a hinge knee prosthesis assembly 100 according to one embodiment of the present invention. Prosthesis 100 includes a tibial component 110, bearing bushing 120, tibial insert 130, bearing or coupling component 140, axle 160, axle bushings 170, and a femoral component 180.

Tibial component 110 generally includes a baseplate 112, stem 114, and keel 116. Baseplate 112 includes a proximal surface 111 that is configured to receive and retain tibial insert 130. Baseplate 112 also includes a distal or bone contact surface 113 disposed opposite proximal surface 111 that is configured to contact and rest upon a resected proximal tibia. As such, bone contact surface 113 is generally planar. However, in some embodiments, bone contact surface 113 may have curved ridges and/or a porous surface to facilitate secure registration with bone.

Stem or protruding portion 114 extends from baseplate 112 and may be sized to fit within an intramedullary canal of a tibia, which may or may not be reamed or otherwise resected to form a larger opening therein. Such fit may be a press fit. Alternatively, stem 114 may be sized to allow a bone cement mantle to be placed between stem 114 and the intramedullary canal and/or may have a porous outer surface to promote bone ingrowth or cement adhesion. An opening 118 extends through baseplate 112 and into stem 114. Opening 118 is sized to receive bearing bushing 120 therein.

Keel 116, which may be located on both lateral and medial sides of baseplate 118, extends between baseplate 118 and stem 114. Keel 116 helps prevent rotation of tibial component 110 when implanted into bone.

Bearing bushing 120 is generally cylindrical and elongate and has an opening 122 extending therein along a longitudinal axis thereof. Opening 122 may extend entirely through bushing 120 or may extend partially therein. Opening 122 is sized to receive a bearing 142 of bearing component 140 (described further below) so that bearing 142 can rotate therein.

Figure 5A:
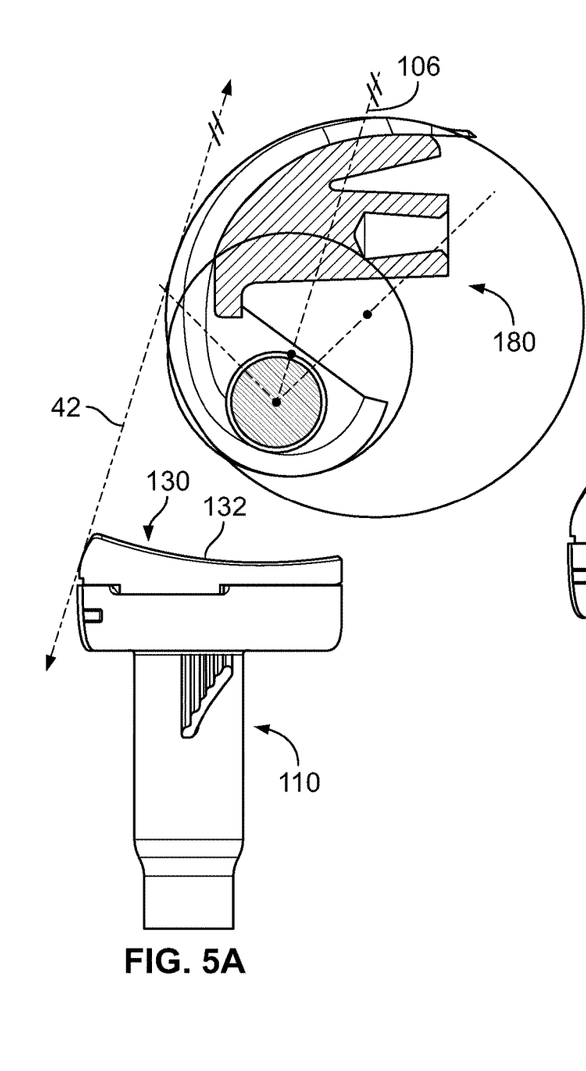
FIG. 5A is an elevational view of the total knee prosthesis of FIG. 2 with certain components removed therefrom and depicting certain geometric features thereof in 90 degrees of flexion.
Figures 5B, 5C:
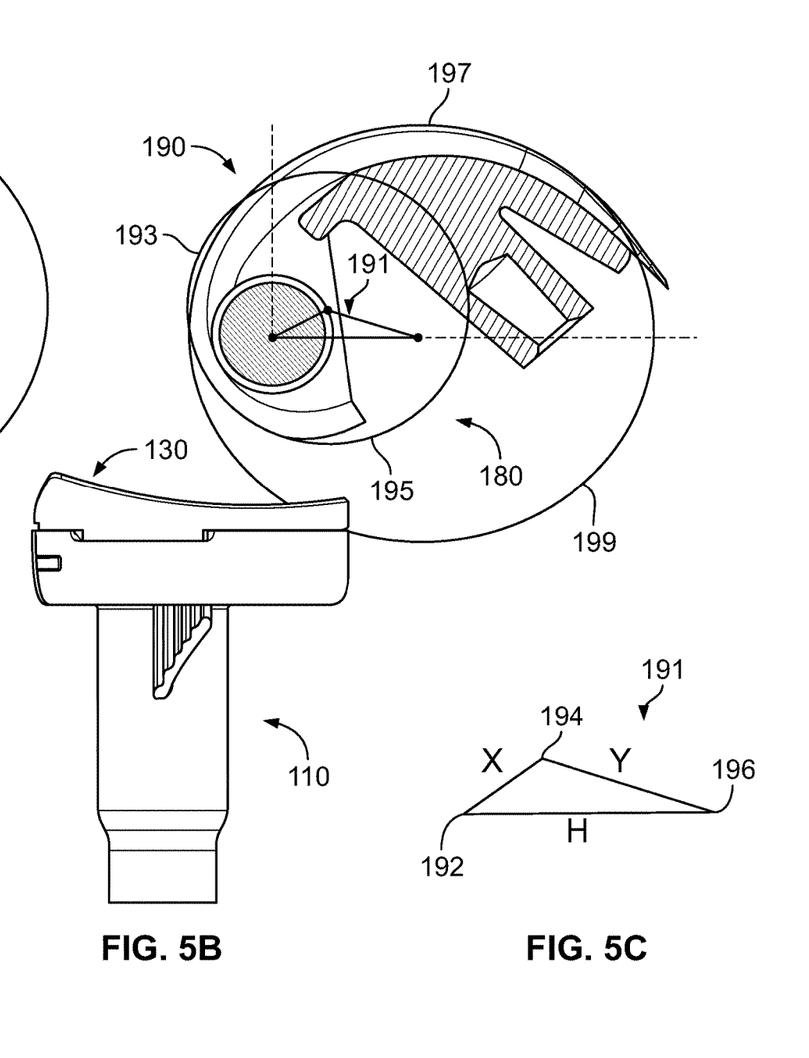
FIG. 5B is an elevational view of the total knee prosthesis of FIG. 2 with certain components removed therefrom and depicting certain geometric features thereof including a flexion triangle in 135 degrees of flexion.
FIG. 5C is a schematic view of the flexion triangle of FIG. 5B.

Tibial insert 130 includes an articular surface 132 that is concave in a sagittal plane such that articular surface 132 is higher at posterior and anterior extents thereof than at a location between such extents (best shown in FIG. 5B). Additionally, articular surface 132 at the anterior extent is generally higher or more proximal than articular surface 132 at the posterior extent. Also, the portion of articular surface 132 extending from the anterior extent toward the posterior extent generally has a steeper slope than the portion of articular surface 132 extending from the posterior extent toward the anterior extent. Moreover, an opening 134 extends through insert 130 sufficiently large to receive bearing 142 of bearing component 140 and for bearing 142 to rotate therein.

Bearing component 140 generally includes an articular portion 144, a bearing 142 extending from articular portion 144, and a head portion 145 extending from articulating portion 144 in a direction opposite that of bearing 142. Bearing 142 is substantially cylindrical and elongate so as to extend through tibial insert 130 and into bearing bushing 120 while being rotatable therein.

Articulating portion 144 includes a convex articular surface 146 corresponding to the concavity of articular surface 132 of tibial component 130. In addition, the thickness of articulating portion 144 is generally greater at a posterior extent thereof than at an anterior extent thereof (best shown in FIG. 3B). This is at least partially due articular surface 146 having a greater slope at an anterior extent thereof than the posterior extent thereof.

Head portion 145 is semi-rectangular and rounded at a proximal end thereof. Head portion 145 is sized to be received within a recess 186 of femoral component 180 (described further below). Head portion 145 also includes a first opening 147 which extends through an anterior surface thereof in an anterior/posterior direction. This first opening 147 is sized to receive a bumper extension 152 of bumper 150. Head portion 145 also includes a second opening 148 which extends through lateral and medial surfaces thereof in a lateral/medial direction transverse to first opening 147. Second opening 148 is preferably disposed more proximal than first opening 147 and is sized to receive axle 160. Additionally, in some embodiments, particularly in embodiments where bumper extension 152 is notched (described further below), first openings 147 may at least partially intersect second opening 148.

Bumper 150 includes a bumper portion 154 and bumper extension 152. Bumper portion 154 has a distal surface 156 configured to rest on a proximal surface of articulating portion 144 of bearing component 140 and a proximal surface 158 configured to abut a distal anterior portion of femoral component 180. Bumper portion 150 may be made from resilient biocompatible materials which can absorb impact from femoral component 180 and compression between femoral component 180 and bearing component 140 over repeated cycles of knee hyperextension.

Bumper extension 152 is substantially cylindrical and sized to extend within first opening 147 of bearing component 140. Bumper extension 152 may also include a rounded notch (not shown) on a proximal surface thereof extending in a direction transverse to a longitudinal axis of bumper extension 152. Such notch may be shaped and positioned along bumper extension 152 so that when extension 152 is inserted into first opening 147 of bearing component 140, axle 160 can be inserted through second opening 148 and be partially disposed within the notch, thereby preventing extension 152 from being removed from first opening 147.

Axle 160 is substantially cylindrical and is sized to be received by axle bushings 170 and second opening 148 of bearing component 140.

Axle bushings 170 are also cylindrical and have openings 172 extending therethrough along a length thereof. Bushings 170 also include a flange 174 at one end thereof. Bushings 170 are sized to fit within transverse openings 184 of femoral component 180 (described further below) while flange 174 is sized to prevent such bushings 170 from passing all the way through transverse openings 184.

Femoral component 180 generally includes inner bone contact surfaces 181, 182, 183 (best shown in FIG. 3A), a stem portion 188, a recess 186, transverse openings 184, and an articular surface 190. Generally TKA prostheses include five inner contact surfaces each corresponding with one of a posterior, anterior, distal, anterior chamfer, and posterior chamfer resected surfaces of a distal femur. While a femoral component according to the present invention can have five of such inner surfaces, femoral component 180 includes three inner contact surfaces 181, 182, 183 (best shown in FIG. 3A) in order to allow for femoral component 180 to have sufficient thickness at a posterior portion thereof for transverse openings 184 to extend therethrough.

Stem portion 188 extends from the second and/or third surfaces 182, 183 and may include an opening therein for receipt of a modular stem (not shown). Stem portion 188 may have a porous outer surface to promote bony ingrowth or cement adhesion.

Recess 186 extends through a posterior portion of femoral component 180 adjacent to stem portion 188 and through first inner surface 181. Recess 186 at least partially defines lateral and medial condylar portions 185 and 187.

Transverse openings 184 extend through lateral and medial condylar portions 184, 187 and intersect recess 186. Openings 184 are aligned such that they are concentric with each other and are sufficiently large to receive axle bushings 170 while being smaller than flanges 174 of axle bushings 170.

Articular surface 190 (best shown in FIGS. 3A & 3B) is curved in a sagittal plane and is primarily configured for articulation with a patella or patellar prosthesis. As such, articular surface 190 may have an intercondylar groove for patellar tracking to prevent lateral or medial subluxation of a patella. However, it should be understood that further reference to articular surface 190 refers to the surface along which a patella articulates. Further detail of articular surface 190 of femoral component 180 is described below.

Figure 3A:
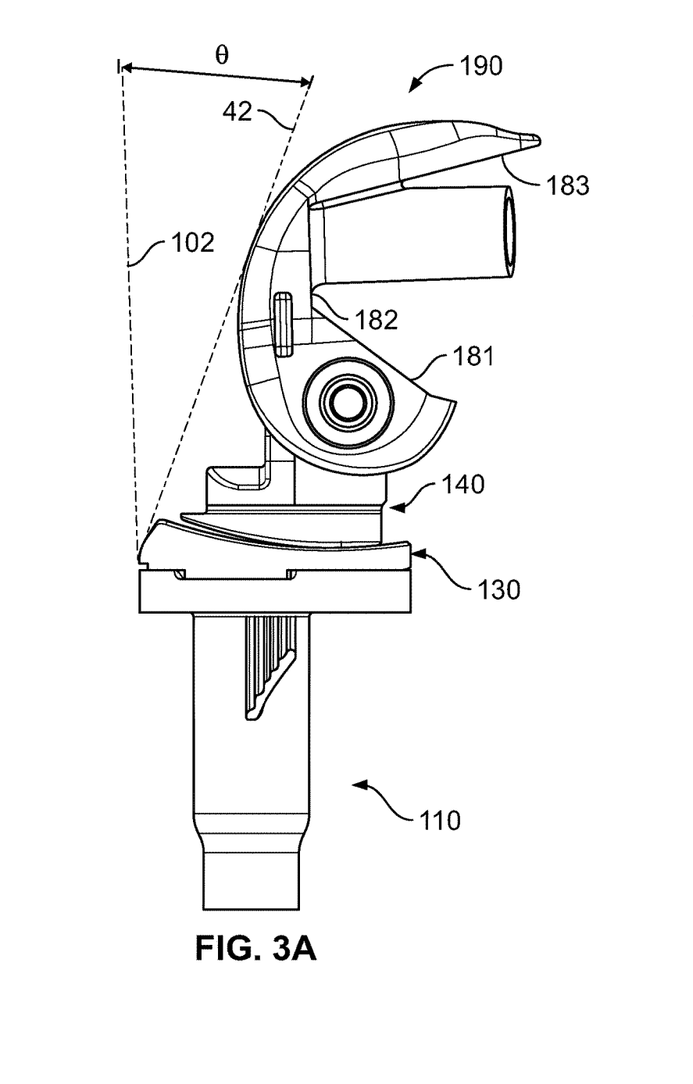
FIG. 3A is an elevational view of the total knee prosthesis of FIG. 2 and a patellar tilt angle in 90 degrees of flexion.
Figure 3B:
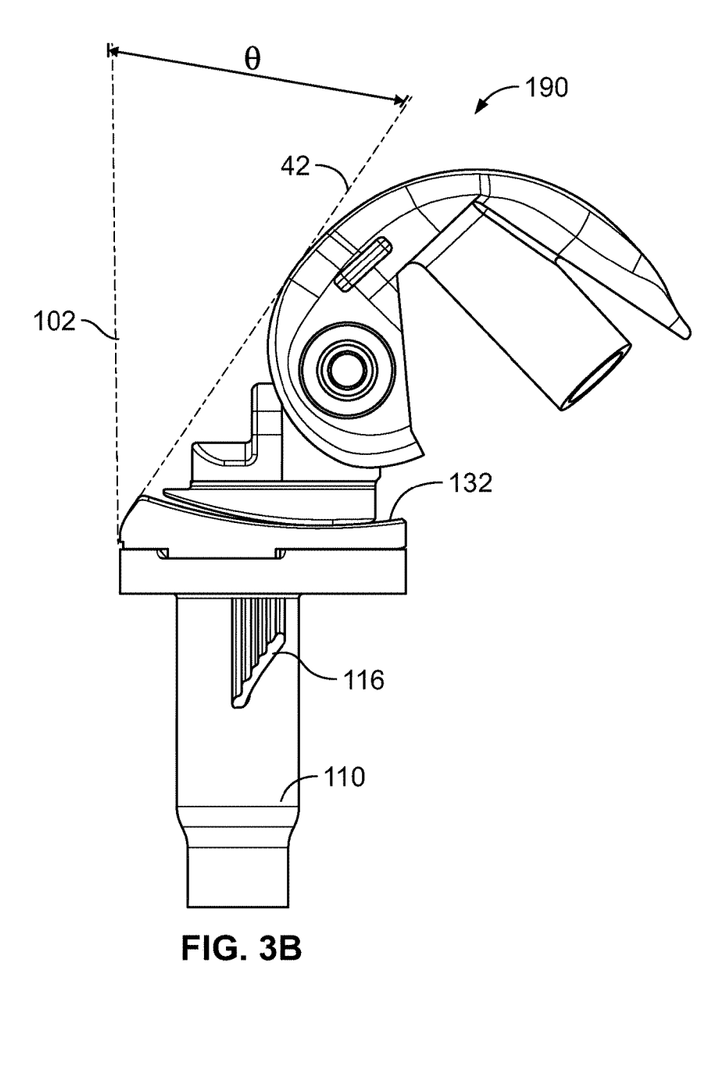
FIG. 3B is an elevational view of the total knee prosthesis of FIG. 2 in 135 degrees of flexion.

FIGS. 3A and 3B depict an assembled prosthesis 100. In a method of assembling prosthesis 100, bearing bushing 120 is inserted into opening 118 of tibial component 110. Tibial insert 130 is then attached to proximal surface 111 of baseplate 112. Thereafter, bearing 142 is inserted through opening 134 in tibial insert 130 and into bearing bushing 120 until articular surface 146 of bearing component 140 contacts articular surface 132 of tibial insert 130. The convexity of articular surface 146 of bearing component 140 and concavity of articular surface 132 of tibial insert 130 help bearing component 140 settle into proper alignment.

Axle bushings 170 are inserted into respective transverse openings 184 of femoral component 180 such that flanges 174 face each other and are disposed adjacent to recess 186. Femoral component 180 is then mounted onto bearing component 140 such that head portion 145 extends into recess 186 of femoral component 180. Once second opening 148 of bearing component 140 is aligned with axle openings 172 and, consequently, transverse openings 184, axle 160 is inserted through axle bushings 170 and bearing component 140, thereby coupling femoral component 180 indirectly to tibial component 110. In other embodiments, bearing component 140 may be rigidly fixed and integrated into tibial component 110. In such embodiments, inserting axle 160 into femoral component 180 and bearing component 140 would directly couple femoral component 180 with tibial component 110.

Thus, in the assembled prosthesis, femoral component 180 can articulate in flexion and extension about a pivot axis (described further below), which is aligned with an axis of axle 160. In addition, bearing component 140 can articulate with bearing bushing 120 and tibial insert 130 about an axis extending along bearing 142. In a natural knee, a tibia can internally and externally rotate about a mechanical axis thereof relative to a femur. When prosthesis 100 is implanted, bearing 142 can rotate within bushing 120 allowing the tibia to rotate in the desired direction relative to femoral component 180 and a femur. As this occurs, articular surface 132 of tibial insert 130 rotates relative to articular surface 146 of bearing component 140, which causes bearing portion 144 to ride up the sloped portions of the tibial insert's articular surface 132. Bearing 142 can translate proximally within bearing bushing 120 to help accommodate bearing components 140 movement up the slope of the insert's articular surface 132. The friction and resistance created by this articulation increases with rotation and helps provide proprioception to the patient and resistance from over-rotation.

Thus, as shown, articular surfaces 132 and 146 of tibial insert 130 and bearing component 140, respectively, articulate during internal and external rotation, and femoral component 180 articulates in flexion and extension via axle 160. However, articular surface 190 of femoral component 180 does not articulate with bearing component 140, tibial insert 130, or tibial component 110. Rather, articular surface 190 of femoral component 180 articulates with a patella, as is described in more detail below. This allows femoral component 180 to be dedicated to natural patellofemoral kinematics.

FIGS. 3A and 3B also depict a patellar tilt angle θ during flexion of prosthesis 100. Patellar tilt angle θ is measured between axis 102 and axis 42. Axis 102 is a superior-inferior axis that represents a starting position of a patellar articular surface in full extension (i.e., zero degrees of flexion). Axis 42 is a tangent axis that lays tangent to articular surface 190 of femoral component 180 and represents a position of the patellar articular surface as it articulates with femoral component 190 during flexion and extension. Such axes 42 and 102 could also represent a patellar tendon and would result in the same patellar tilt angle θ.

As mentioned above, in a natural knee, the maximum patellar tilt angle is about 35 degrees in deep flexion. At 90 degrees of flexion of prosthesis 100, as shown in FIG. 3A, the patellar tilt angle θ is about 20 degrees. Most current hinge knee prostheses reach the 35 degree maximum at 90 degrees of flexion. As such, many of the current hinge knee prostheses limit patient range of motion to 90 degrees of flexion.

At 135 degrees of flexion of prosthesis 100, as shown in FIG. 3B, the patellar tilt angle θ is about 35 degrees or less. Thus, in deep flexion, the patellar tilt angle θ mimics a natural patellar tilt angle. This differs from many of the current hinge knee prostheses, which would reach about 40 degrees of patellar tilt at 135 degrees of flexion, and can impose significant tension on the patella tendon risking damage to the tendon and patella and resulting in painful flexion for the patient.

FIGS. 4 and 5A-5C depict geometric features and dimensions of femoral component 180 and prosthesis 100, generally, that allows for prosthesis 100 to obtain a maximum patellar tilt angle θ of about 35 degrees in deep flexion. As shown, articular surface 190 is curved in a sagittal plane and includes an anterior portion 197 and posterior portion 193 (best shown in FIG. 5B). Posterior portion 193 is defined by a first circle 195 having a first flexion center 194 and first flexion radius ($R_{1st}$). Anterior portion 197 is defined by a second flexion circle 199 having a second flexion center 196 and second flexion radius ($R_{2nd}$). Second flexion radius $R_{2nd}$ is larger than first flexion radius $R_{1st}$. Anterior portion 197 and posterior portion 193 intersect each other and posterior portion 193 is generally positioned such that a patella articulates with posterior portion 193 in deep flexion (i.e., at about 115 degrees of flexion or more). As such, a patella articulates with anterior portion 197 before deep flexion.

Figure 4:
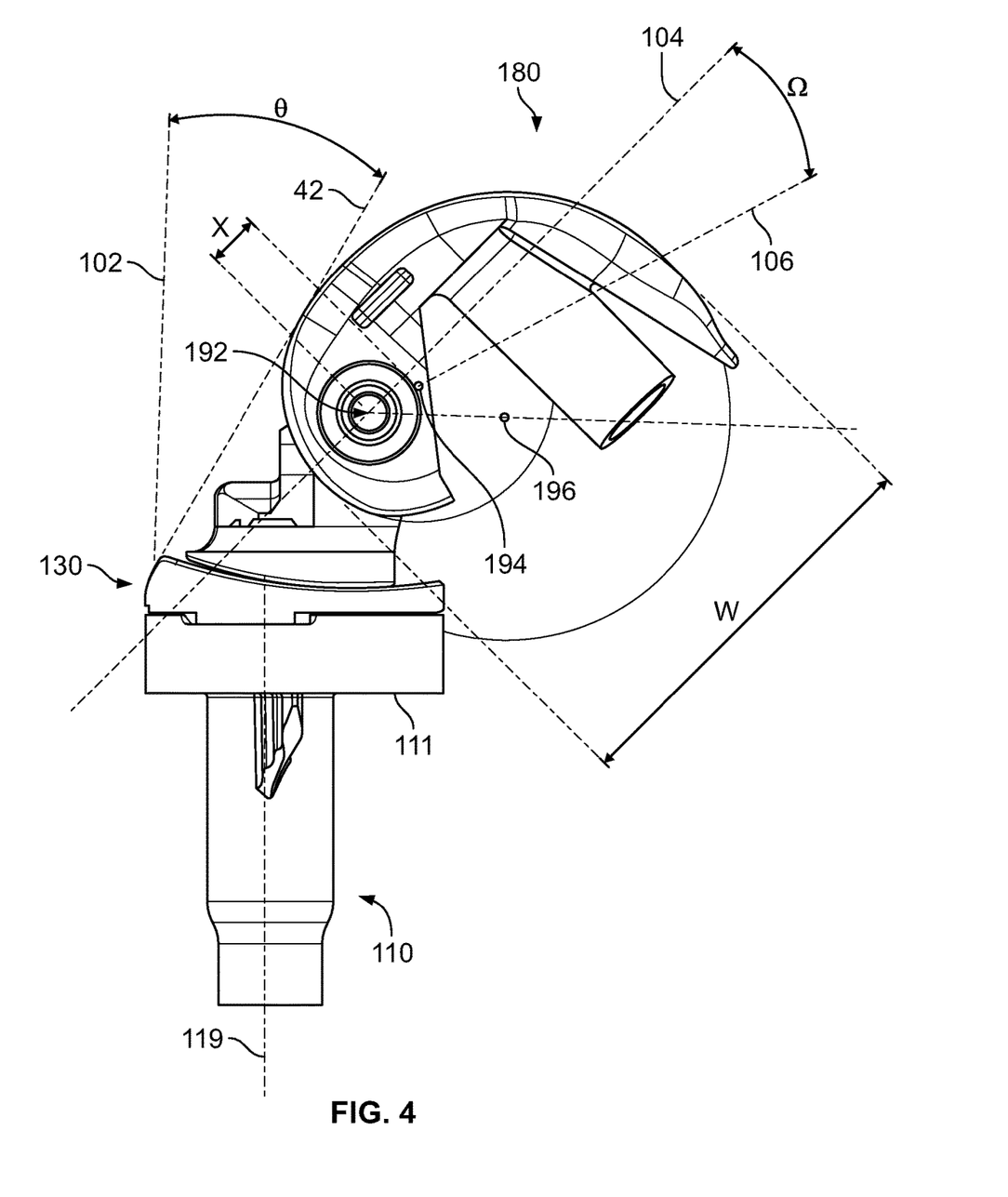
FIG. 4 is an elevational view of the total knee prosthesis of FIG. 2 and various dimensions thereof in 135 degrees of flexion.

FIG. 4 illustrates a location of first flexion center 194 and various other dimensions that facilitate natural patellofemoral kinematics. In particular, femoral component 180 has an anterior-posterior width W. In addition, first flexion center 194 is offset a distance X from a pivot center 192 about which femoral component 100 flexes and extends. As mentioned above, this pivot center 192 is aligned with a longitudinal axis of axle 160. First flexion radius $R_{1st}$ is about 16-28 mm and is substantially equal to (1/3)(W). X is about 6-12 mm and is substantially equal to ($R_{1st}$) (C), where C is a constant substantially equal to 0.4. Thus, distance X is a function of the anterior-posterior width W of femoral component 180 and is also a function of the first flexion radius $R_{1st}$. This is true across multiple sizes of femoral component 180.

Also shown in FIG. 4 is a reference angle Ω, which is defined as the angle between axis 104 and axis 106. Axis 104 is an axis that extends through pivot center 192 and a theoretical tibial tubercle about which the patella rotates. Axis 106 is an axis that extends through first flexion center 194 and pivot center 192. Reference angle Ω is substantially equal to patellar tilt angle θ. Thus, where a deep flexion patellar tilt angle of about 35 degrees is desired, reference angle Ω is set to about 35 degrees and first flexion center 194 is positioned along axis 106 and offset distance X from pivot center 192. Thus, X and Q are polar coordinates, with pivot center 192 as the origin, determining the location of first flexion center 194 so that posterior portion 193 of articular surface 190 can be properly located and dimensioned so that prosthesis 100 can mimic natural patellofemoral kinematics, particularly in deep flexion.

The relationship between axis 106 and tangent axis and, therefore, the relationship between first flexion center 194 and pivot center 192 is further illustrated in FIG. 5A. As shown, when prosthesis 100 is at 90 degrees of flexion, axis 42 is parallel to axis 106.

Pivot center 192 may be positioned relative to tibial component 110, which itself is implanted in a proximal tibia in a relative position to a tibial tubercle. Pivot center 192 may be located relative to certain features of tibial component 110, which may be dependent on size of baseplate 112, in order to help position pivot center 192 and, therefore, articular surface 190 relative to a tibial tubercle to facilitate natural patellofemoral kinematics. For example, pivot center 192 may be offset posteriorly from a longitudinal axis 119 (best shown in FIG. 4) of tibial stem 114 a distance of about 15-25 mm. Additionally, pivot center 192 may be offset a distance of about 35-55 mm from distal surface 111 of baseplate 112.

FIGS. 5B and 5C further illustrate first flexion center 194 relative to pivot center 192 and also illustrates the positioning of second flexion center 196. As shown, second flexion center 196 is offset from first flexion center 194 and pivot center 192. These three centers form apexes of a flexion triangle 191 in which distance Y is the distance between first and second flexion centers 194, 196, and distance H, which is the hypotenuse of flexion triangle 191, is the distance between pivot center 192 and second flexion center 196. In one embodiment, distance Y may be about 7-21 mm, and distance H may be about 15-35 mm. In addition, the angle between X and H may be about 15 to 60 degrees. This flexion triangle 191 and the dimensions thereof, help locate first and second flexion centers 194, 196 and, therefore, articular surface 190, relative to pivot center 192 to facilitate natural patellofemoral kinematics of prosthesis 100.

Thus, when implanted, patellar articulation varies when articulating along each portion 193 and 197 of articular surface 190. When a patella articulates along anterior portion 197, tilt angle θ generally increases up to about 35 degrees. At this point, patellar articulation transitions to posterior portion 193 where the maximum tilt angle θ of about 35 degrees is maintained throughout deep flexion. This is a substantial benefit as it allows a patient with prosthesis 100 to achieve greater range of motion of their replaced knee.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A total knee prosthesis, comprising:
a tibial component having a baseplate portion and a protruding portion extending from the baseplate portion;
an axle connectable to the tibial component; and
a femoral component having an articular surface and an opening for receipt of the axle, the opening defining a pivot center about which the femoral prosthesis rotates with respect to the tibial component, the articular surface having anterior and posterior portions, the posterior and anterior portions each being curved so as to define respective first and second flexion centers, the first flexion center being offset from the posterior portion by a first flexion radius, the second flexion center being offset from the anterior portion by a second flexion radius, wherein the first flexion center is positioned relative to the pivot center and to the second flexion center so that when the total knee prosthesis is implanted, a patella articulating with the articular surface of the femoral component has a maximum patellar tilt angle of about 35 degrees when the total knee prosthesis is articulated between 90 and 135 degrees of flexion.

2. The total knee prosthesis of claim 1, wherein the first flexion center is offset from the pivot center a distance equal to a product of the first flexion radius and a constant that is equal to 0.4.

3. The total knee prosthesis of claim 1, wherein the femoral component has an anterior-posterior dimension defined by a distance between anterior and posterior extents of the prosthesis, and the first flexion radius is equal to one-third of the anterior-posterior dimension.

4. The total knee prosthesis of claim 1, wherein the first flexion radius is about 16-28 mm.

5. The total knee prosthesis of claim 1, wherein the protruding portion of the tibial component defines a longitudinal axis, and the pivot center is about 15-25 mm from the longitudinal axis in an anterior-posterior direction when the tibial component and femoral component are coupled together via the axle.

6. The total knee prosthesis of claim 5, wherein the baseplate portion includes a bone contact surface for contacting a proximal tibial resected surface, the bone contact surface being about 35-55 mm from the pivot center in a superior-inferior direction when the tibial component and femoral component are coupled together via the axle.

7. The total knee prosthesis of claim 1, wherein the first flexion center is positioned such that a line segment intersecting the pivot center and first flexion center is substantially parallel to a patella tendon when the total knee prosthesis is implanted and articulated to about 90 degrees of flexion.

8. The total knee prosthesis of claim 1, wherein the articular surface includes an anterior portion having a second flexion radius defining a second flexion surface.

9. The total knee prosthesis of claim 8, wherein the first flexion center is about 7-21 mm offset in the sagittal plane from the second flexion center.

10. The total knee prosthesis of claim 8, wherein the pivot center, first flexion center, and second flexion center form vertices of a triangle having a hypotenuse extending between the pivot center and second flexion center, a first line segment extending between the pivot center and first flexion center, and a second line segment extending between the first and second flexion centers.

11. The total knee prosthesis of claim 10, wherein an angle formed between the first line segment and hypotenuse is about 15-60 degrees.

12. The total knee prosthesis of claim 10, wherein the hypotenuse is about 15-35 mm.

13. The total knee prosthesis of claim 10, wherein, when the total knee prosthesis is implanted into a knee joint comprised of a femur and a tibia and articulated beyond 90 degrees of flexion, a reference angle formed between the first line segment and a line intersecting the pivot center and a tibial tubercle of the tibia determines a patellar tilt angle of a patella about the tibial tubercle with respect to a superior-inferior axis of the tibia.

14. The total knee prosthesis of claim 13, wherein the reference angle and patellar tilt angle are substantially equal.

15. The total knee prosthesis of claim 14, wherein the reference angle is about 35 degrees or less.

16. The total knee prosthesis of claim 1, further comprising a coupling component having a bearing, a head portion, and an articulating portion, the bearing being receivable by the tibial component, the head portion engageable to the femoral component and having an opening extending therethrough for receipt of the axle, the articulating portion disposed between the head portion and bearing and having a curved inferior surface for sliding articulation with a superior surface of the tibial component.

17. A total knee prosthesis comprising:
a tibial component for implantation into a tibia of a knee joint;
a coupling component configured to engage the tibial component and having a head portion defining an opening therethrough for receipt of an axle; and
a femoral component for implantation into a femur of a knee joint defining a recess for receipt of the head portion and a transverse opening for receipt of the axle and having an articular surface having a first curved portion and a second curved portion, the opening defining a pivot center about which the femoral component flexes and extends, the first curved portion defining a first radius and a first center, the second curved portion defining a second radius and a second center,
wherein the pivot center and first and second centers are positioned with respect to each other such that when the total knee prosthesis is implanted into the knee joint, the articular surface is positioned with respect to a tibial tubercle of the tibia such that a tilt angle of a patella about the tibial tubercle achieves and maintains about 35 degrees or less with respect to a superior-inferior axis of the tibia as the patella articulates with the articular surface through flexion of the femoral component relative to the tibial component of between 90 and 135 degrees.

18. The total knee prosthesis of claim 17, wherein the first center is offset from the pivot center in a sagittal plane a distance equal to a product of a constant and the first radius, the constant being 0.4 and the first radius being about 16-28 mm.

19. The total knee prosthesis of claim 18, wherein the first radius is equal to one-third of an anterior-posterior dimension of the formal component that extends between anterior and posterior extents of the femoral component.

20. The total knee prosthesis of claim 18, wherein the second center is offset from the pivot center in a sagittal plane a distance substantially equal to 15-35 mm.

21. The total knee prosthesis of claim 20, wherein the first center and second center are offset from one another a distance substantially equal to 7-21 mm.

22. A total knee prosthesis, comprising:
a tibial component having a baseplate portion and a protruding portion extending from the baseplate portion;
an axle connectable to the tibial component; and
a femoral component having an articular surface and an opening for receipt of the axle, the opening defining a pivot center about which the femoral prosthesis rotates, the articular surface having a posterior portion having a first flexion radius defining a first flexion center, the first flexion radius being equal to one-third of an anterior-posterior width of the femoral component.

\* \* \* \* \*